United States Patent [19]

Charmot

[11] Patent Number: 4,948,739
[45] Date of Patent: Aug. 14, 1990

[54] COMPACT POLYMER/METAL COMPOSITE PARTICLES, AQUEOUS DISPERSIONS THEREOF, PREPARATION AND USE IN BIOLOGICAL APPLICATIONS

[75] Inventor: Dominique Charmot, Paris, France

[73] Assignee: Rhone-Poulenc Chimie, Courbevoie, France

[21] Appl. No.: 177,390

[22] Filed: Apr. 4, 1988

[30] Foreign Application Priority Data

Apr. 3, 1987 [FR] France ............... 87 04684

[51] Int. Cl.$^5$ ............... B01J 13/02; C08K 3/08; G01N 33/546
[52] U.S. Cl. ............... 436/533; 252/62.54; 424/469; 427/213.31; 427/213.36; 428/402.24; 436/534; 523/211; 524/780; 524/785
[58] Field of Search ............... 427/213.31, 213.36; 428/402.24; 252/62.54; 424/469; 523/211; 436/533, 534; 524/780, 785; 502/402

[56] References Cited

U.S. PATENT DOCUMENTS

| 3,228,881 | 1/1966 | Thomas | 252/62.54 |
|---|---|---|---|
| 4,197,220 | 4/1980 | Rembaum et al. | 260/8 |
| 4,252,671 | 2/1981 | Smith | 252/430 |
| 4,252,672 | 2/1981 | Smith | 252/430 |
| 4,252,673 | 2/1981 | Smith | 252/430 |
| 4,252,674 | 2/1981 | Smith | 252/430 |
| 4,252,675 | 2/1981 | Smith | 252/430 |
| 4,252,676 | 2/1981 | Smith | 252/430 |
| 4,252,677 | 2/1981 | Smith | 252/430 |
| 4,252,678 | 2/1981 | Smith | 252/430 |
| 4,339,337 | 7/1983 | Tricot et al. | 252/62.54 |
| 4,447,475 | 5/1984 | Lubbock et al. | 427/213.31 |

FOREIGN PATENT DOCUMENTS 0038730 10/1981 European Pat. Off. .

OTHER PUBLICATIONS

Munro et al., Nonporous Magnetic Materials as Enzyme Supports: Studies with Immobilized Chymotrypsin, XIX Biotechnology and Bioengineering 101–124, (1977).
Hess et al., Polymers for Stabilization of Colloidal Cobalt Particles, 10 J. Appl. Poly. Sci. 1915–1927, (1966).
Griffiths et al., The structure, magnetic characterization, and oxidation of colloidal iron dispersions, 50(11), J. Appl. Phy. 7108–7115, (Nov. 1979).

Primary Examiner—Richard D. Lovering
Attorney, Agent, or Firm—Finnegan, Henderson, Farabow, Garrett, and Dunner

[57] ABSTRACT

Compact polymer/metal composite particles, sized or unsized, in which the metal is in the form of crystallites encapsulated in a polymer matrix. The composite particles may be prepared by introducing a metal complex into a swollen polymer in an organic liquid which is a solvent for the metal complex, followed by thermal decomposition of the metal complex and removal of the swelling organic liquid. The composite particles may be used in biological applications.

38 Claims, No Drawings

COMPACT POLYMER/METAL COMPOSITE PARTICLES, AQUEOUS DISPERSIONS THEREOF, PREPARATION AND USE IN BIOLOGICAL APPLICATIONS

FIELD OF THE INVENTION

The present invention relates to compact composite particles based on a polymer matrix containing metal inclusions, such composite particles preferably being sized. The present invention also relates to dispersions of these composite particles, particularly in water, to the process for preparing them and to their use in biological applications.

BACKGROUND OF THE INVENTION

Polymer particles impregnated with metal in the zero valence state are described in U.S. Pat. No. 4,197,220. The particles disclosed therein are, for example, hydrophilic and microporous polyvinylpyridine particles which are impregnated with metal by complexing with metal ions, followed by a reduction with a water-soluble reducing agent such as a borohydride. The microporosity of the support, and the state of division of the metal precipitated inside the pores, render such particles an advantageous material for the catalytic hydrogenation of olefins. Other applications are also mentioned, such as X-ray electron probe methods (since such particles are electron-dense) and protein separation techniques.

The disadvantage possessed by such particles arises from the fact that they are porous and contain metal at the surface.

In applications involving biological substances (such as proteins), cells or drugs, it is very important that the metal be completely encapsulated in the polymer of the particle and absent from the surface.

Thus, in enzymatic engineering, it is known that certain enzymes are inhibited on contact with metal ions originating from the support. For example, it has been shown that chymotrypsin immobilized on nickel powder rapidly loses its activity (Munro et al., *Nonporous Magnetic Materials as Enzyme Supports: Studies with Immobilized Chymotrypsin*, XIX Biotechnology and Bioengineering 101–124 (1977)).

Another undesirable effect relates to the phenomena of irreversible adsorption of hormones (T3, T4) or steroids on magnetic supports based on iron oxide, which adsorption interferes considerably with assays of the radioimmunoassay (RIA) type.

Finally, in cell culture, the presence of metal ions derived from the support may also disturb cell adhesion.

The preparation of metal colloids in an organic medium has been known since the work of Hess and Parker (Hess et al., *Polymers for Stabilization of Colloidal Cobalt Particles*, 10 J. Appl. Poly. Sci. 1915–1927 (1966)) and J. R. Thomas (U.S. Pat. No. 3,228,881), as well as T. W. Smith (U.S. Pat. Nos. 4,252,671 through 4,252,678, inclusive). The technique involves thermally decomposing an organo-metallic coordination compound, particularly a metal carbonyl compound, in an organic solution of polymer. A colloidal dispersion is obtained for example, a ferro-fluid comprising $10^{-6}$ to $10^{-5}$ mm metal particles in an organic solvent. The polymer is adsorbed at the surface of the metal particles, and provides for the colloidal stability of the suspension. When such a ferro-fluid is exposed to the ambient atmosphere, the metal particles, although confined in a hydrophobic organic phase, oxidize rapidly and lose their magnetic properties (Griffiths et al., *The structure, magnetic characterization, and oxidation of colloidal iron dispersions*, 50(11) J. Appl. Phy. 7108–7115 (Nov. 1979)). Moreover, as a result of their size, generally less than 300 angstroms, these metal particles, on which the polymer has a surfactant effect, cannot be separated from the organic solvent (by magnetization, in the case of an iron or cobalt ferro-fluid) without destroying the colloidal stability. Finally, these particles of metal, subjected to a surfactant effect, are completely incompatible with aqueous media, and accordingly cannot be used in the applications described above.

European Pat. No. 38,730 describes latices of particles of hydrophobic vinylaromatic polymer containing a magnetizable filler. These particles are obtained by dispersion of the magnetic filler in an organic phase composed of an organo-soluble initiator, the vinylaromatic monomer and/or a water-insoluble organic compound, followed by mixing of the dispersion with an aqueous solution of emulsifier, homogenization and, finally, polymerization. Such a process has the disadvantage that it can be used only for the preparation of latices of unsized particles—that is, particles possessing a spread particle size distribution.

When used as a solid phase in biological applications, the particles of such latices should preferably be sized.

SUMMARY OF THE INVENTION

The subject of the present invention is a process which makes it possible to prepare compact polymer/metal composite particles, sized or otherwise, in which all, or essentially all, of the metal is completely encapsulated (included) in the polymer, and in which the metal retains its zero valence state as well as its magnetic properties (if the metal in question is magnetizable, such as iron or cobalt) with the passage of time.

The metal of the composite particles of the invention is substantially no longer accessible at the surface of the particles, and is, therefore, no longer in a position to interact with substances anchored at the surface of the polymer.

DESCRIPTION OF THE INVENTION

The subject of the present invention is a process for preparing compact polymer/metal composite particles, comprising the following steps:

(1) dispersing, in an organic liquid solvent for a metal-carbonyl, -organocarbonyl or -hydrocarbon complex that can be thermally decomposed at a temperature below the boiling point of the organic liquid, anhydrous particles of polymer bearing nucleophilic sites which can be coordinated with the metal complex, the size of the polymer particles preferably being on the order of 0.1 micron to 1 mm, and more preferably on the order of 0.5 to 100 microns, the nature of the polymer constituting the polymer particles being such that the polymer particles swell, in the presence of the organic liquid, to a volume such that they become accessible to molecules of the metal complex while remaining insoluble in the organic liquid, preferably to a volume that is 0.1 to 50 times, and more preferably 3 to 10 times, their original volume;

(2) introducing a metal-carbonyl, -organocarbonyl or -hydrocarbon complex which is soluble in the organic liquid into the dispersion of swollen particles of polymer obtained in step (1), preferably according to a ratio by weight of metal in the metal complex: polymer on the order of 0.5:100 to 200:100, more preferably on the order of 0.5:100 to 90:100, most preferably on the order of 3:100 to 35:100, and thermally decomposing the metal complex, with the proviso that the decomposition takes place under a reducing atmosphere when the metal complex is a metal-hydrocarbon complex; and (3) removing the organic liquid from the swollen polymer to obtain the compact polymer/metal composite particles.

Optionally, the compact composite particles thereby obtained are redispersed in a liquid that does not swell the polymer.

The polymer employed may be any crosslinked polymer bearing nucleophilic sites capable of coordinating with the carbonyl, organocarbonyl or hydrocarbon complexes of the metal. The polymer must additionally be capable of swelling in the presence of an organic liquid which is a solvent for one of the metal complexes, to a volume such that it becomes accessible to the molecules of the metal complex.

Preferred crosslinked polymers include copolymers derived from:

30 to 99%, and preferably 50 to 95%, by weight of at least one monoethylenic monomer which does not coordinate with the metal complex.

Representative monoethylenic monomers include:
styrene and its derivatives (such as vinyl toluene and ethylvinylbenzene)
the esters and amides of (meth)acrylic acid (such as methyl methacrylate, butyl acrylate and (meth)acrylamide)
(meth)acrylic acid and monoethylenic diacids (such as maleic acid and itaconic acid)
vinylpyrrolidone
vinyl esters (such as vinyl acetate and vinyl propionate)
vinyl and vinylidene chlorides;
0 5 to 50%, preferably 2 to 20%, by weight of at least one crosslinkable polyethylenic monomer which does not coordinate with the metal complex.
Representative polyethylenic monomers include:
divinylbenzene and its derivatives
conjugated dienes (such as butadiene)
polyallyl compounds (such as tetraallylethylene)
the (meth)acrylates of polyols (such as ethylene glycol dimethacrylate)
methylenebis(acrylamide)
bis(acrylamido)acetic acid; and
0.5 to 30%, preferably 3 to 30%, by weight of at least one nucleophilic monomer which can be coordinated with the metal complex.
Representative nucleophilic monomers which can be coordinated include:
vinylpyridines (such as 2-vinylpyridine, 4-vinylpyridine, 2-methyl-5-vinylpyridine and 2,5-divinylpyridine)
di(ethyl)aminoalkyl (meth)acrylates
di(ethyl)aminoalkyl (meth)acrylamides
allylamine
ethylenimine
(meth)acrylonitrile
1-vinylimidazole
dialkylaminomethylstyrenes.

The copolymers may be obtained according to the conventional techniques of emulsion polymerization, microsuspension polymerization, suspension polymerization or free-radical dispersion polymerization.

The polymer particles employed in the first step of the process of the invention may have a polydisperse or monodisperse particle size distribution—that is, they can be sized or unsized. The term "sized" as used herein means of uniform size, with a standard deviation of the diameter of less than about 5%.

The nature and the level of crosslinking of the polymer enables the particles employed to swell perceptibly while remaining insoluble in the organic liquid. The level of crosslinking is, as such, preferably low.

The organic liquid is chosen in such a way that it swells the polymer particles, does not spontaneously decompose the metal-carbonyl, -organocarbonyl or -hydrocarbon complexes and is inert with respect to the latter. It is preferable that the organic liquid should not be an electron donor.

For improved industrial production, it is preferable that the boiling point of the organic liquid be above 80° C., preferably above 100° C., at atmospheric pressure, in order to avoid the use of pressurized plants.

Representative organic liquids which can favorably be employed include aromatic compounds (such as toluene, ethylbenzene and xylenes), chlorinated aromatic compounds (such as mono-, di- and trichlorobenzene), aliphatic and cyclic hydrocarbons (such as heptane, decane, cyclohexane and decalin) dialkyl ethers, alcohols (such as pentanol and cyclohexanol) and esters (such as methyl propionate).

The dispersion of the polymer particles in the organic liquid may be accomplished without difficulty. The presence of an emulsifying agent is not necessary, since the considerable swelling of the polymer promotes mechanisms of stabilization by steric repulsion.

The concentration by weight of polymer particles in the organic liquid may vary, preferably between 1 and 35%, according to the swelling capacity of the polymer. A concentration on the order of 1 to 20% by weight is most preferable to preserve a moderate viscosity of the medium which facilitates, for example the subsequent evolution of carbon monoxide when the complex employed is a metal carbonyl.

Representative metal-carbonyl, -organocarbonyl or -hydrocarbon complexes which may be employed in the second step of the process of the instant invention include carbonyl complexes, organocarbonyl complexes of the aliphatic, cycloaliphatic or aromatic type, and hydrocarbon complexes of the aliphatic or cycloaliphatic type, of the metals of Groups VIa, VIIa and VIII of the Periodic Classification of the elements, in particular those of the following metals: chromium, molybdenum, tungsten, manganese, rhenium, iron, cobalt, rhodium, iridium, nickel, osmium, and ruthenium.

Exemplary such complexes include:
the following metal-carbonyl complexes: $Cr(CO)_6$; $Mo(CO)_6$; $W(CO)_6$; $(Mn)_2(CO)_{10}$; $(Re)_2(CO)_{10}$; $Fe(CO)_5$; $(Fe)_2(CO)_9$; $(Fe)_3(CO)_{12}$; $(Co)_2(CO)_8$; $(Co)_4(CO)_{12}$; $Ni(CO)_4$; $(Rh)_6(CO)_{12}$; $(Rh)_4(CO)_{12}$; $(Ir)_4(CO)_{12}$; $(Os)_3(CO)_{12}$; $(Ru)_3(CO)_{12}$
the following organocarbonyl complexes:
(methylcyclopentadienyl)$Mn(CO)_3$;
(cyclopentadienyl)$Mn(CO)_3$;
(cyclopentadienyl)$Co(CO)_2$;
(cyclopentadienyl)$Re(CO)_3$
the following hydrocarbon complexes:
(di-n5-cyclopentadienyl)Ni or Fe The introduction of the metal complex in the second step is preferably carried out at room temperature, or at least at a temperature below that of the decomposition of the metal complex, in order to avoid a sudden evolution of carbon monoxide (for example, in the case of the carbonyl complexes).

The complex is preferably introduced in toto from the beginning of the second step. However, another embodiment of the invention comprises introducing from 15% to 50% of the metal complex at the beginning, and then adding the remainder of the metal complex in continuous fashion over a period of 0.5 to 3 hours.

The thermal decomposition operation is carried out at a temperature above the decomposition temperature of the metal complex. This operation is preferably carried out at a temperature in the vicinity of that of the boiling point of the organic liquid, in order to promote the removal, for example, of carbon monoxide. The progress of this operation may be followed by measuring, for example, the volume of carbon monoxide evolved.

The thermal decomposition operation may be carried out under a reducing atmosphere in order to avoid a possible oxidation of the metal. This operation can, for example, be performed under conditions of bubbling hydrogen through the reaction medium.

When the complex employed is a metal-hydrocarbon complex, for example (di-n$^5$-cyclopentadienyl)Ni or Fe (known as nickelocene and ferrocene), it is essential to perform this operation under a reducing atmosphere provided, for example, by bubbling hydrogen through the reaction medium. It is preferably performed, for example, under a hydrogen pressure of 5 to 10 bars.

When the organic liquid swells the polymer particles only when it is brought to a certain temperature, known as the theta temperature (this being the case, in particular, with cyclohexane or decahydronaphthalene as regards copolymers rich in styrene units), it is clearly understood that the temperature at which the second step is carried out must be above this theta temperature.

Taking these considerations into account, the preferred temperature range for the thermal decomposition reaction is generally between 80° C. and 200° C.

The time required for the complete, or essentially complete, decomposition of the complex naturally depends on the temperature employed and the thermal stability of the metal complex. In general, this operation lasts at least 1 hour and does not exceed 24 hours.

During this step, the complex added to the dispersion of swollen polymer particles first dissolves in the molecular state outside and inside the particles swollen with organic liquid. When the whole preparation is brought to a temperature above that of decomposition of the complex (preferably corresponding to the refluxing temperature of the organic liquid), the complex decomposes. The precipitation of the metal in the zero valence state is initiated inside the particles by virtue of the nucleophilic sites of the polymer. The nuclei thus formed, in turn, catalyze the decomposition of the complex. Preferably, no metal formation is observed in the organic liquid phase outside the particles.

The metal content of the particles obtained at the end of this second step, the size of the crystallites and their distribution can be controlled by adjusting the working conditions.

The thermal decomposition of the complexes is initiated at the nucleophilic sites, and the density of the metal nuclei is directly related to the number of nucleophilic sites. Thus, for a given quantity of metal introduced, the higher the concentration of sites, the smaller the metal crystallites.

The working conditions described above enable a crystallite size preferably on the order of $10^{-6}$ to $10^{-4}$ mm, most preferably on the order of $3 \times 10^{-6}$ to $3 \times 10^{-5}$ mm, to be produced. The content of metal thereby incorporated may preferably range up to 67% by weight, and more preferably up to 26% by weight, based on the weight of the particles.

The third step is that of removal of the swelling organic liquid. The object of this step is to encapsulate the metal within the polymer, by changing the particles of polymer from the swollen state to the compact state. Preferably, in the compact state, the size of the composite particles obtained almost corresponds to that of the starting polymer particles.

The swelling organic liquid may be removed from the reaction medium by conventional liquid/solid separation means, such as centrifugation, filtration or magnetization (when the metal contained in the particles is magnetizable).

The swelling organic liquid remaining in the particles may then be removed by drying.

Another method of removal of the swelling organic liquid includes, after separation of the particles from the reaction medium, washing the particles using a liquid that does not swell the polymer and which is miscible with the swelling organic liquid. This washing operation can be repeated several times.

The choice of the non-swelling liquid is naturally linked to the nature of the polymer. Thus, when the polymer is rich in styrene units, the most common non-swelling liquids are monohydric alcohols such as methanol, ethanol and isopropanol, and diols such as monoethylene or propylene glycol.

If desired, the dispersed composite particles thereby obtained may be isolated by any known means, such as centrifugation, filtration or magnetization (when the metal contained in the composite particles is magnetizable).

An especially advantageous embodiment of the process of the invention involves the preparation of latices (aqueous dispersions) of the composite particles.

This especially preferred embodiment comprises carrying out the removal of the swelling organic liquid (third step) by separation of the particles obtained in the second step by, preferably, centrifugation, filtration or magnetization (when the metal contained is magnetized), followed by washing of the separated particles using an intermediate non-swelling liquid which is miscible with the swelling organic liquid and with water (it being possible for this washing operation to be repeated several times). This embodiment comprises performing a further operation of separation of the composite particles thereby obtained, and a still further operation of washing the composite particles thereby separated with water (it being possible for this washing operation to be repeated several times).

The intermediate non-swelling liquid must be miscible with the swelling liquid and with water, and must not be reactive with the metal contained in the particles.

Thus, when the swelling organic liquid is an aromatic compound (such as toluene or xylene), the intermediate non-swelling medium may be chosen from monohydric alcohols (such as methanol and isopropanol) and diols (such as monoethylene or propylene glycol).

The redispersion in the intermediate non-swelling liquid or in water is facilitated by adding surfactants.

The term "surfactant" is understood to mean all substances of an amphiphilic nature, such as anionic emulsifiers (for example, alkyl sulfates, alkyl sulfonates, alkylaryl sulfonates, dialkylsulfosuccinates, and fatty acid salts), cationic emulsifiers (for example, cetylpyridinium salts, alkylbenzylammonium salts, and fatty amine salts) and nonionic emulsifiers (for example, ethoxylated nonylphenols, ethoxylated sorbitan monooleate, and ethylene oxide/propylene oxide copolymers), and also polymers which are soluble in the suspension medium and capable of adsorbing to the surface of the particles. The latter may include polyvinyl alcohol, cellulose derivatives (such as hydroxyalkyl celluloses), polyvinylpyrrolidone, polyacrylic acid, copolymer resins (such as styrene/maleic, methyl vinyl ether/maleic, and acrylic/maleic resins), cationic polymers (such as polyallylamine) or, alternatively, natural macromolecules (such as gelatin or bovine serum albumin).

The subject of the present invention also includes polymer/metal composite particles, preferably sized, in which all, or essentially all, of the metal is completely encapsulated in the polymer. The term "sized" means of uniform size, with a standard deviation of the diameter of less than about 5%.

Preferred polymer/metal composite particles of the invention may be described as follows:

compact, sized, having a uniform size on the order of 0.1 micron to 1 mm, preferably on the order of 0.5 to 100 microns, and comprising:

a matrix based on a polymer bearing nucleophilic sites which can be coordinated with a metal complex, the quantity of nucleophilic sites which can be coordinated representing on the order of 0.5 to 30%, preferably on the order of 3 to 30%, of the weight of the polymer;

and, encapsulated in the matrix, crystallites of a metal at the zero valence state, the size of the crystallites being on the order of $10^{-6}$ to $10^{-4}$ mm, preferably on the order of $3 \times 10^{-6}$ to $3 \times 10^{-5}$ mm;

the quantity of encapsulated metal representing approximately 0.5 to 67%, preferably 3 to 26%, of the weight of the composite particles;

the metal being derived from carbonyl, organocarbonyl or hydrocarbon metal complexes which are thermally unstable; and the nature of the polymer being such that the latter is capable of swelling by 0.1 to 50 times, preferably by 3 to 10 times, its original volume in the presence of an organic liquid which is a solvent for the metal-carbonyl, metal-organocarbonyl or metal-hydrocarbon complexes, the boiling point of the organic liquid being above the temperature of decomposition of the metal complexes.

The metal of the composite particles can be any metal, magnetizable or otherwise, capable of forming carbonyl, organocarbonyl or hydrocarbon complexes which can be thermally decomposed, where appropriate under a reducing atmosphere, to the metal state of zero valence. Exemplary metals include those of Groups VIa, VIIa and VIII of the Periodic Classification of the elements, such as chromium, molybdenum, tungsten, manganese, rhenium, iron, cobalt, rhodium, iridium, nickel, osmium, and ruthenium.

The polymer constituting the matrix may be any crosslinked polymer bearing nucleophilic sites capable of coordinating with the carbonyl, organocarbonyl or hydrocarbon complexes of the metal. The polymer must additionally be capable of swelling in the presence of an organic liquid which is a solvent for one of the metal complexes, to a volume such that it becomes accessible to the molecules of the metal complex.

Polymers which may constitute the matrix of the composite particles forming the subject of the invention include those already mentioned above.

A particularly preferred embodiment of the compact polymer/metal composite particles forming the subject of the present invention are sized particles having a uniform size on the order of 0.1 micron to 1 mm, preferably on the order of 0.5 to 100 microns, and comprising:

99.5 to 33%, preferably 99.5 to 43%, more preferably 97 to 74%, by weight of a matrix based on a polymer derived from 30 to 99%, preferably 50 to 95%, by weight of at least one monoethylenic monomer which does not coordinate with the metal complex, 0.5 to 50%, preferably 2 to 20%, by weight of at least one crosslinkable polyethylenic monomer which does not coordinate with the metal complex and 0.5 to 30%, preferably 3 to 30%, by weight of at least one nucleophilic monomer which can be coordinated with the metal complex;

and, encapsulated in the matrix, on the order of 0.5 to 67%, preferably on the order of 3 to 26%, by weight of crystallites of a metal of Group VIa, VIIa or VIII of the Periodic Classification of the elements, in the zero valence state, the size of the crystallites being on the order of $10^{-6}$ to $10^{-4}$ mm, preferably on the order of $3 \times 10^{-6}$ to $3 \times 10^{-5}$ mm.

The sized composite particles may be prepared according to the procedure described above, employing sized particles of polymer bearing nucleophilic sites which can be coordinated in the first step.

Another embodiment of the invention includes aqueous dispersions or latices of the composite particles of the invention, preferably of the sized composite particles described above. The dry extract content of the dispersions (that is, the content of sized composite particles) preferably ranges from 1 to 50% by weight, more preferably from 2–50% by weight and most preferably from 5 to 20% by weight based on the weight of the dispersion.

The latices of sized composite particles may be prepared according to known methods, by dispersion in water of the sized composite particles described above. Emulsifiers are preferably present in such latices.

Preferably, these latices are obtained according to the process for preparing latices described above, employing sized particles of polymer in the first step.

The polymer/metal composite particles, as they are or in aqueous dispersion, which form the subject of the invention can be used as a solid phase in biological applications, such as in diagnostic tests.

When the metal is magnetizable, the magnetizable properties of the particles may be turned to good account to separate them easily from the incubation medium and to speed up the washing stages in heterogeneous tests of the radioimmunoassay or enzyme-immunoassay type.

Mention may also be made of the use of these products as a support for the immobilization of, for example, enzymes, cells or antigens/antibodies in biotechnology; and in medical imaging.

Other applications of these aqueous dispersed particles relate to conductive inks, paints and glues, as well as to magnetic recording.

The examples which follow are illustrative, and should not be considered as limiting either the scope or spirit of the invention.

EXAMPLE 1

25 g of cobalt carbonyl are added to 175 g of dry toluene. This solution is stored shielded from the air.

The following are introduced into a 100-ml 3-necked round-bottomed flask placed in an oil bath, equipped with a nitrogen inlet and an anchor-type stirring device, linked to a light solvent connector and surmounted by a condenser connected to a device for measuring the carbon monoxide evolved:

18 g of toluene, and 2 g of sized particles (average diameter 2.1 microns±0.1 micron) consisting of a styrene/divinylbenzene/4-vinylpyridine copolymer (respective % by weight, 85:10:5), which corresponds to a dry extract of 10% by weight of crosslinked copolymer in the toluene.

Nitrogen is bubbled through the dispersion obtained.

The stirring is adjusted to 100 rpm and the temperature of the oil bath is taken to a sufficient temperature (130° C.) to bring the toluene to a boil and to carry away the final traces of water.

After a 3 hour distillation, the reactor is cooled to room temperature. The nitrogen inlet is removed.

4.15 g of previously prepared solution of cobalt carbonyl (which corresponds to a ratio by weight of metal/particles of 0.089) are then introduced using a syringe.

A first gaseous evolution of 30 ml of carbon monoxide, corresponding to the displacement of the CO (of the metal carbonyl) by the pyridine units of the particles, is observed immediately.

The temperature of the bath is then brought to 130° C. in the 110° C.). The refluxing of the toluene speeds up the evolution of carbon monoxide (56% of the theoretical total volume is evolved from the time when the solvent is brought to reflux).

After further heating for 4 hours at 130° C., 95% of the theoretical volume of carbon monoxide has been collected. The dispersion has changed from an orangered appearance to a deep black appearance.

The reaction medium is cooled to room temperature.

The suspended swollen particles thereby obtained are attracted in the presence of a magnet. The supernatant is completely transparent and colorless; its infrared analysis reveals no trace of cobalt carbonyl or of polynuclear cobalt complexes.

The spherules are recovered by magnetic separation. The residual solvent is removed in a rotary evaporator at 40° C. under 2700 pascals, and then at 60° C. under 1600 pascals.

On the black powder obtained, the cobalt content is analyzed by conversion to inorganic form and assay of the cobalt ions by atomic absorption; its content is equal to 8.9% (theory: 8.9%).

The distribution of the metal within the particles is visualized by transmission electron microscopy on ultra-thin sections produced by mixing the spherules with an EPON 812 inclusion resin (an epoxy-type resin marketed by BALZERS) and sectioning the composite obtained using an ultramicrotome. It is found that the metal is distributed uniformly throughout the volume of the composite particles, in the form of crystals measuring $3 \times 10^{-6}$ to $15 \times 10^{-6}$ mm.

Examination of these same particles by scanning microscopy shows that the impregnation with the metal has not affected the appearance of the spherules, their surface remaining perfectly smooth and spherical.

1 g of these composite particles is added to 50 ml of an aqueous solution of sodium lauryl sulfate having a concentration of 1 g/l. After 30 s of ultrasonic treatment, a stable suspension is obtained.

These composite particles may be separated from the medium in less than 10 min by applying a laboratory magnet ($8 \times 10^{-6}$ Tesla) laterally to the bottle containing the dispersion.

When stored in the form of an aqueous suspension, these particles retain their magnetic properties, even after 6 months of storage.

EXAMPLES 2 TO 10

The meaning of the abbreviations appearing in Tables I to IV is as follows:

S : styrene
DVB : divinylbenzene
MMA : methyl methacrylate
4-VP : 4-vinylpyridine
NVI : N-vinylimidazole
DEAMS : diethylaminomethylstyrene
AN : acrylonitrile The operation described in Example 1 is repeated, employing: sized particles of the copolymer defined in Tables I to IV, in the presence of the swelling liquid ("solvent") appearing in these tables; the respective quantities of copolymer and of swelling liquid also appear in these tables ("dry extract");

the metal carbonyl appearing in Tables I to IV, dissolved in the swelling liquid; the respective quantities of metal carbonyl and of copolymer appear in these tables ("metal/particles").

The conditions of temperature and time of the thermal decomposition operation appear in Tables I to IV.

The temperature indicated corresponds to that of the inside of the flask and the time corresponds to the time during which the flask is heated in order to maintain the indicated temperature inside the flask (it does not include the time necessary for bringing the flask to the indicated temperature).

The characteristics of the composite particles obtained appear in Tables I to IV. ($\phi$ represents size).

EXAMPLE 11

The operation described in Examples 1 to 10 is repeated, employing unsized particles of copolymer.

The nature of the constituents employed, their respective quantities, the working conditions and the characteristics of the composite particles obtained appear in Table IV.

EXAMPLE 12

The thermal decomposition operation described in Example 1 is repeated.

The suspended swollen particles obtained are attracted in the presence of a magnet. The supernatant is removed and replaced by ethanol (50 ml per gram of particles).

This operation is repeated three times.

The final supernatant is removed and replaced by an aqueous solution of sodium lauryl sulfate having a concentration of 1 g/l (50 ml per gram of particles). This operation is repeated three times.

The final traces of toluene trapped within the particles are removed by azeotropic distillation at 110° C. for one hour.

A latex of composite particles whose properties appear in Table IV is thereby obtained.

TABLE I

| EXAMPLE | 1 | 2 | 3 |
|---|---|---|---|
| Crosslinked copolymer | | | |
| composition | | | |
| S % | 85 | 65 | 90 |
| DVB % | 10 | 10 | 5 |
| MMA % | | | |
| 4-VP % | 5 | 25 | 5 |
| NVI % | | | |
| DEAMS % | | | |
| AN % | | | |
| ∅ particles μm | 2.1 ± 0.1 | 2.1 ± 0.1 | 2.1 ± 0.1 |
| dry extract % | 10 | 9 | 9 |
| Solvent | toluene | toluene | toluene |
| Metal carbonyl | Co2(CO)8 | Co2(CO)8 | Co2(CO)8 |
| metal/particle (weight) | 0.089 | 0.089 | 0.077 |
| Working conditions | | | |
| temperature °C. | 110 | 110 | 133 |
| time h | 4 | 5 | 6.25 |
| Composite Particles | | | |
| ∅ μm | 2.1 ± 0.1 | 2.1 ± 0.1 | 2.1 ± 0.1 |
| % metal | 8.9 | 8.7 | 7.5 |
| ∅ crystallites mm × $10^{-6}$ | 3–15 | <2 | 3–13 |

TABLE II

| EXAMPLE | 4 | 5 | 6 |
|---|---|---|---|
| Crosslinked copolymer | | | |
| composition | | | |
| S % | 90 | 75 | 85 |
| DVB % | 10 | 10 | 5 |
| MMA % | | | |
| 4-VP % | 5 | 15 | |
| NVI % | | | 10 |
| DEAMS % | | | |
| AN % | | | |
| ∅ particles μm | 2.1 ± 0.1 | 2.1 ± 0.1 | 2.1 ± 0.1 |
| dry extract % | 8.4 | 11.3 | 8.7 |
| Solvent | toluene | chlorobenzene | xylene |
| Metal carbonyl | Co2(CO)8 | Fe(CO)5 | Co2(CO)8 |
| metal/particle (weight) | 0.178 | 0.133 | 0.091 |
| Working Conditions | | | |
| temperature °C. | 110 | 150 | 135 |
| time h | 6.16 | 22 | 6.5 |
| Composite Particles | | | |
| ∅ μm | 2.1 ± 0.1 | 2.1 ± 0.1 | 2.1 ± 0.1 |
| % metal | 18 | 13 | 8.7 |
| ∅ crystallites mm × $10^{-6}$ | — | — | 3–8 |

TABLE III

| EXAMPLE | 7 | 8 | 9 |
|---|---|---|---|
| Crosslinked copolymer | | | |
| composition | | | |
| S % | 85 | 85 | 60 |
| DVB % | 10 | 5 | 10 |
| MMA % | | | 25 |
| 4-VP % | | | 5 |
| NVI % | | | |
| DEAMS % | 5 | | |
| AN % | | 10 | |
| ∅ particles μm | 2.1 ± 0.1 | 2.1 ± 0.1 | 0.95 ± 0.05 |
| dry extract % | 8.7 | 11.1 | 9 |
| Solvent | toluene | xylene | chlorobenzene |
| Metal carbonyl | Co(CO)8 | Fe(CO)5 | Cr(CO)6 |
| metal/particle (weight) | 0.9 | 0.114 | 0.05 |
| Working Conditions | | | |
| temperature °C. | 110 | 135 | 150 |
| time h | 5.5 | 7.25 | 10 |
| Composite Particles | | | |
| ∅ μm | 2.1 ± 0.1 | 2.1 ± 0.1 | 0.95 ± 0.05 |
| % metal | 9 | 11.1 | 5 |
| ∅ crystallites mm | — | — | — |

TABLE IV

| EXAMPLE | 10 | 11 | 12 |
|---|---|---|---|
| Crosslinked copolymer | | | |
| composition | | | |
| S % | 85 | 85 | 85 |
| DVB % | 10 | 10 | 10 |
| MMA % | | | |
| 4-VP % | 5 | 5 | 5 |
| NVI % | | | |
| DEAMS % | | | |
| AN % | | | |
| ∅ particles μm | 9.7 ± 0.5 | 52 ± 23 | 2.1 ± 0.1 |
| dry extract % | 9 | 9 | 10 |
| Solvent | toluene | toluene | toluene |
| Metal carbonyl | Co2(CO)8 | Co2(CO)8 | Co2(CO)8 |
| metal/particle (weight) | 0.05 | 0.05 | 0.089 |
| Working Conditions | | | |
| temperature °C. | 110 | 110 | 110 |
| time h | 4 | 4 | 4 |
| Composite particles | | | |
| ∅ μm | 9.7 ± 0.5 | 52 ± 23 | 2.1 ± 0.1 |
| % metal | 4.9 | 5 | 8.9 |
| ∅ crystallites mm × $10^{-6}$ | — | 3–15 | 3–15 |

We claim:

1. A process for preparing compact polymer/metal composite particles comprising the steps of:
   (1) dispersing, in an organic liquid solvent for a metal-carbonyl, -organocarbonyl or -hydrocarbon complex that can be thermally decomposed at a temperature below the boiling point of said organic liquid, anhydrous particles of polymer bearing nucleophilic sites which can be coordinated with said metal complex, the nature of said polymer being such that said polymer particles swell, in the presence of said organic liquid, to a volume such that said polymer particles become accessible to molecules of said metal complex while remaining insoluble in said organic liquid;
   (2) introducing a metal-carbonyl, -organocarbonyl or -hydrocarbon complex which is soluble in said organic liquid into the dispersion of swollen polymer particles obtained in said step (1), and thermally decomposing said metal complex, with the proviso that said decomposition takes place under a reducing atmosphere when said metal complex is a metal-hydrocarbon complex; and
   (3) removing said organic liquid from said swollen polymer particles to obtain said compact polymer/metal composite particles.

2. The process of claim 1, wherein the size of said polymer particles in said step (1) is from 0.1 micron to 1 mm.

3. The process of claim 1, wherein said polymer particles swell by 0.1 to 50 times their original volume in the presence of said organic liquid.

4. The process of claim 1, wherein the ratio by weight of metal in said metal complex : polymer, employed in said step (2), is from 0.5:100 to 200:100.

5. The process of claim 1, wherein said composite particles obtained are redispersed in a liquid that does not swell said polymer.

6. The process of claim 1, wherein, after removal of said organic liquid in said step (3), said composite particles obtained are washed using an intermediate non-swelling liquid which is miscible with said organic liquid and with water, and are then separated from said intermediate non-swelling liquid and dispersed in water by washing with water.

7. The process of claim 1, wherein said composite particles obtained are sized having a uniform size of from 0.1 micron to 1 mm and wherein:
said polymer particles employed in said step (1) are sized having a uniform size of from 0.1 micron to 1 mm, the nature of said polymer constituting said polymer particles being such that said polymer particles swell by 0.1 to 50 times their original volume in the presence of said organic liquid;
said polymer forms the matrix of said composite particles, and comprises 0.5–30% by weight of nucleophilic sites which can be coordinated with said metal complex; and
the ratio by weight of metal in said metal complex : polymer employed in said step (2) is from 0.5:100 to 200:100,
whereby said composite particles obtained comprise crystallites of said metal at the zero valence state encapsulated in said matrix, the size of said crystallites being from $10^{-6}$ to $10^{-4}$ mm, and the quantity of encapsulated metal represents about 0.5 to 67% by weight of said composite particles.

8. The process of claim 7, wherein said composite particles obtained are redispersed in a liquid that does not swell said polymer.

9. The process of claim 7, wherein said composite particles obtained are washed using an intermediate non-swelling liquid which is miscible with said organic liquid and with water, said non-swelling liquid is removed; and said composite particles are then dispersed in water by washing with water until a concentration of 1 to 50% by weight of said particles in the water is obtained.

10. The process of claim 1, wherein, in said step (1), the size of said polymer particles is from 0.5 to 100 microns.

11. The process of claim 1, wherein, in said step (1), said polymer particles swell by 3 to 10 times their original volume in the presence of said organic liquid.

12. The process of claim 1, wherein, in said step (2), the ratio by weight of metal in said metal complex : polymer employed is from 3:100 to 35:100.

13. The process of claim 1, wherein said polymer comprises 30 to 99% by weight of at least one monoethylenic monomer which does not coordinate with said metal complex, 0.5 to 50% by weight of at least one crosslinkable polyethylenic monomer which does not coordinate with said metal complex and 0.5 to 30% by weight of at least one nucleophilic monomer which can be coordinated with said metal complex.

14. The process of claim 13, wherein said polymer comprises:
50 to 95% by weight of at least one monoethylenic monomer which does not coordinate with said metal complex;
2 to 20% by weight of at least one crosslinkable polyethylenic monomer which does not coordinate with said metal complex; and
3 to 30% by weight of at least one nucleophilic monomer which can be coordinated with said metal complex.

15. The process of claim 13, wherein said monoethylenic monomer is selected from the group consisting of styrene, styrene derivatives, esters and amides of acrylic and methacrylic acid, acrylic acid, methacrylic acid, monoethylenic diacids, vinylpyrrolidone, vinyl esters, vinyl chloride and vinylidene chloride.

16. The process of claim 13, wherein said polyethylenic monomer is selected from the group consisting of divinylbenzene, divinylbenzene derivatives, conjugated dienes, polyallyl compounds, acrylates and methacrylates of polyols, methylenebis(acrylamide) and bis(acrylamido)acetic acid.

17. The process of claim 13, wherein said nucleophilic monomer is selected from the group consisting of vinylpyridine, di(ethyl)aminoalkyl acrylates and -methacrylates, di(ethyl)aminoalkylacrylamides and -methacrylamides, allylamine, ethylenimine, acrylonitrile, methacrylonitrile, 1-vinylimidazole and dialkylaminomethylstyrenes.

18. The process of claim 1, wherein said organic liquid is an aromatic compound, optionally chlorinated, an aliphatic or cycloaliphatic hydrocarbon, a dialkyl ether, an alcohol or an ester, said organic liquid having a boiling point above the decomposition temperature of said metal complex.

19. The process of claim 1, wherein the concentration of said polymer particles in said organic liquid in said step (1) is from 1 to 35% by weight.

20. The process of claim 1, wherein said metal complex is a carbonyl complex, an organocarbonyl complex of the aliphatic, cycloaliphatic or aromatic type, or a hydrocarbon complex of the aliphatic or cycloaliphatic type, and wherein the metal of said metal complex is a Group VIa, VIIa or VIII metal of the Periodic Classification of the elements.

21. The process according to claim 20, wherein said metal complex is selected from the group consisting of $Cr(CO)_6$, $Mo(CO)_6$, $W(CO)_6$, $(Mn)_2(CO)_{10}$, $(Re)_2(CO)_{10}$, $Fe(CO)_5$, $(Fe)_2(CO)_9$, $(Fe)_3(CO)_{12}$, $(Co)_2(CO)_8$, $(Co)_4(CO)_{12}$, $Ni(CO)_4$, $(Rh)_6(CO)_{12}$, $(Rh)_4(CO)_{12}$, $(Ir)_4(CO)_{12}$, $(Os)_3(CO)_{12}$, $(Ru)_3(CO)_{12}$, (methylcyclopentadienyl)Mn(CO)$_3$, (cyclopentadienyl)Mn(CO)$_3$, (cyclopentadienyl)Co(CO)$_2$, (cyclopentadienyl)Re(CO)$_3$, (di-n$^5$-cyclopentadienyl)Ni and (di-n$^5$-cyclopentadienyl)Fe.

22. The process of claim 1, wherein said thermal decomposition is carried out at a temperature of from 80° to 200° C.

23. The process of claim 1, wherein said thermal decomposition is carried out at a temperature in the vicinity of the boiling point of said organic liquid.

24. An aqueous dispersion of the composite particles produced by the process of claim 1.

25. The aqueous dispersion of claim 24, wherein said composite particles comprise from 1–50% by weight of said dispersion.

26. The method of using the composite particles produced by the process of claim 1 wherein said particles are employed as a solid phase in a biological application.

27. Polymer/metal composite particles, having a size of from 0.1 micron to 1 mm, said composite particles comprising 99.5 to 33% by weight of a matrix based on a copolymer derived from (a) 0.5 to 30% by weight of at least one monomer bearing nucleophilic sites which can be coordinated with a metal complex selected from the group consisting of metal-carbonyl, -organocarbyl and -hydrocarbon complexes, (b) 30 to 99% by weight of at least one monoethylenic monomer which does not coordinate with said metal complex, and (c) 0.5 to 50% by weight of at least one crosslinkable polyethylenic monomer which does not coordinate with said metal complex and, encapsulated in said matrix, 0.5 to 67% by weight of crystallites of a metal of Group VIa, VIIa, or vIII of the Periodic Classification of the elements in the zero valence state derived from said metal complex, the nature of said copolymer being such that particles of said copolymer are capable of swelling by 0.1 to 50 times their volume, in the presence of an organic liquid which is a solvent for said metal complex, said swollen volume of said particles being such that said copolymer particles become accessible to the molecules of said metal complex while remaining insoluble in said organic liquid, said organic liquid having a boiling point above the temperature of decomposition of said metal complex, and wherein said composite particles are compact and sized, and wherein the size of said metal crystallites is from $10^{-6}$ to $10^{-4}$ mm.

28. The composite particles of claim 27, wherein said metal retains its zero valence state and, if magnetizable, its magnetic properties upon exposure of said composite particles to ambient conditions.

29. The composite particles of claim 27, wherein the quantity of said nucleophilic sites in said matrix represents from 3 to 30% of the weight of said polymer.

30. The composite particles of claim 27, wherein said composite particles have a uniform size of from 0.5 to 100 microns.

31. The composite particles of claim 27, wherein said particles comprise 97 to 74% by weight of said matrix and 3 to 26% by weight of said metal.

32. The composite particles of claim 25, wherein the size of said metal crystallites is from $3 \times 10^{-6}$ to $3 \times 10^{-5}$ mm.

33. The composite particles of claim 27, wherein said compact and sized composite particles have a uniform size from 0.1 micron to 1 mm.

34. An aqueous dispersion of the composite particles of claim 27.

35. The aqueous dispersion of claim 34, wherein said composite particles comprise 1-50% by weight of said dispersion.

36. The method of using the composite particles of claim 27, wherein said particles are employed as a solid phase in a biological application.

37. The method of claim 36, wherein said composite particles, as they are or in an aqueous dispersion, are employed as a solid phase in a diagnostic test.

38. Compact polymer/metal sized composite particles of a uniform size of from 0.1 micron to 1 mm, comprising:

99.5 to 33% by weight of a matrix based on a copolymer derived from 30 to 99% by weight of at least one monoethylenic monomer which does not coordinate with a metal complex, 0.5 to 50% by weight of at least one crosslinkable polyethylenic monomer which does not coordinate with a metal complex and 0.5 to 30% by weight of at least one nucleophilic monomer which can be coordinated with a metal complex;

and, encapsulated in said matrix, from 0.5 to 67% by weight of crystallites of a metal of Group VIa, VIIa or VIII of the Periodic Classification of the elements in the zero (valence state, the size of said crystallites being from $10^{-6}$ to $10^{-4}$ mm.

* * * * *

UNITED STATES PATENT AND TRADEMARK OFFICE
CERTIFICATE OF CORRECTION

PATENT NO. : 4,948,739
DATED : August 14, 1990
INVENTOR(S) : Dominique Charmot

It is certified that error appears in the above-identified patent and that said Letters Patent is hereby corrected as shown below:

Claim 27, Column 15, Line 9, "vIII" should be --VIII--.

Signed and Sealed this

Tenth Day of November, 1992

Attest:

DOUGLAS B. COMER

Attesting Officer

Acting Commissioner of Patents and Trademarks